(12) United States Patent
Okada et al.

(10) Patent No.: US 12,315,155 B2
(45) Date of Patent: May 27, 2025

(54) INFORMATION PROCESSING APPARATUS, INFORMATION PROCESSING METHOD, INFORMATION PROCESSING PROGRAM, AND INFORMATION PROCESSING SYSTEM

(71) Applicant: fcuro inc., Osaka (JP)

(72) Inventors: Naoki Okada, Osaka (JP); Shusuke Inoue, Osaka (JP)

(73) Assignee: feuro inc., Osaka (JP)

( * ) Notice: Subject to any disclaimer, the term of this patent is extended or adjusted under 35 U.S.C. 154(b) by 14 days.

(21) Appl. No.: 17/926,832

(22) PCT Filed: Apr. 12, 2022

(86) PCT No.: PCT/JP2022/017558
§ 371 (c)(1),
(2) Date: Nov. 21, 2022

(87) PCT Pub. No.: WO2022/224869
PCT Pub. Date: Oct. 27, 2022

(65) Prior Publication Data
US 2023/0342920 A1   Oct. 26, 2023

(30) Foreign Application Priority Data
Apr. 23, 2021   (JP) .................................. 2021-073175

(51) Int. Cl.
*G06T 7/00* (2017.01)
*A61B 5/00* (2006.01)
(Continued)

(52) U.S. Cl.
CPC .......... *G06T 7/0012* (2013.01); *A61B 5/4842* (2013.01); *A61B 5/743* (2013.01);
(Continued)

(58) Field of Classification Search
CPC ................. G06T 7/0012; G06T 11/001; G06T 2207/10081; G06T 2207/10088;
(Continued)

(56) References Cited

U.S. PATENT DOCUMENTS

| | | | | |
|---|---|---|---|---|
| 2004/0101176 A1* | 5/2004 | Mendonca | ............ | G06T 7/0012 382/199 |
| 2006/0013454 A1* | 1/2006 | Flewelling | .............. | G06T 11/00 382/128 |

(Continued)

FOREIGN PATENT DOCUMENTS

| | | |
|---|---|---|
| JP | 2004173910 A | 6/2004 |
| JP | 2012247879 A | 12/2012 |

(Continued)

OTHER PUBLICATIONS

Miller, Shannon, "How to Read DEXA Scan Results", published at https://www.compositionid.com/blog/dexa/how-to-read-dexa-scan-results/ as of Mar. 21, 2019 (also saved at archive.org as of Aug. 9, 2020) (Year: 2019).*

(Continued)

*Primary Examiner* — William A Beutel
(74) *Attorney, Agent, or Firm* — Erise IP, P.A.

(57) ABSTRACT

The present invention provides an information processing apparatus, an information processing method, an information processing program, and an information processing system that facilitates recognition of an identification result. An information processing apparatus has a first acquisition unit configured to acquire measurement data obtained by measurement of a physical condition of a patient, a second acquisition unit configured to acquire, using a first disease identification model generated by machine learning that uses teaching data labeled with first classifications of body portions included in measurement data obtained by measurement of a physical condition of a human and presence of a (Continued)

disease in the body portions, the first classification of a body portion in the measurement data acquired by the first acquisition unit and presence of a disease in the body portions, and a display unit configured to display the presence of the disease in the body portions that is acquired by the second acquisition unit in accordance with the first classification.

16 Claims, 9 Drawing Sheets

(51) Int. Cl.
*G06T 11/00* (2006.01)
*G06V 10/764* (2022.01)
*G16H 50/30* (2018.01)

(52) U.S. Cl.
CPC .......... *G06T 11/001* (2013.01); *G06V 10/764* (2022.01); *G16H 50/30* (2018.01); *G06T 2207/10081* (2013.01); *G06T 2207/10088* (2013.01); *G06T 2207/20081* (2013.01); *G06T 2207/20092* (2013.01); *G06T 2207/30004* (2013.01)

(58) Field of Classification Search
CPC . G06T 2207/20081; G06T 2207/20092; G06T 2207/30004; A61B 5/4842; A61B 5/743; G06V 10/764; G16H 50/30
See application file for complete search history.

(56) References Cited

U.S. PATENT DOCUMENTS

| | | | |
|---|---|---|---|
| 2008/0104116 A1* | 5/2008 | Van Hoe | G06V 10/764 |
| 2010/0141654 A1 | 6/2010 | Neemuchwala et al. | |
| 2014/0281961 A1* | 9/2014 | Baker | G16H 30/40 |
| | | | 715/705 |
| 2018/0122517 A1* | 5/2018 | Bessette | G16H 20/30 |
| 2019/0057504 A1 | 2/2019 | Kobayashi | |
| 2020/0379620 A1* | 12/2020 | Horiuchi | G16H 30/20 |
| 2020/0410677 A1 | 12/2020 | Keshwani | |
| 2021/0035687 A1* | 2/2021 | Yi | A61B 5/7435 |

FOREIGN PATENT DOCUMENTS

| | | |
|---|---|---|
| JP | 2015-227882 A | 12/2015 |
| JP | 2019-033966 A | 3/2019 |
| JP | 2021029387 A | 3/2021 |
| JP | 2021-058272 A | 4/2021 |
| KR | 102108401 B1 | 5/2020 |
| WO | 2019176806 A1 | 9/2019 |
| WO | 2020146024 A1 | 7/2020 |

OTHER PUBLICATIONS

PCT Patent Application No. PCT/JP2022/017558 International Search Report and Written Opinion.
Japanese Patent Application 2022-567772, Notice of Reason for Refusal, issued Oct. 26, 2023.
Japanese Patent Application 2022-567772, Notice of Refusal, issued Jul. 5, 2023.

* cited by examiner

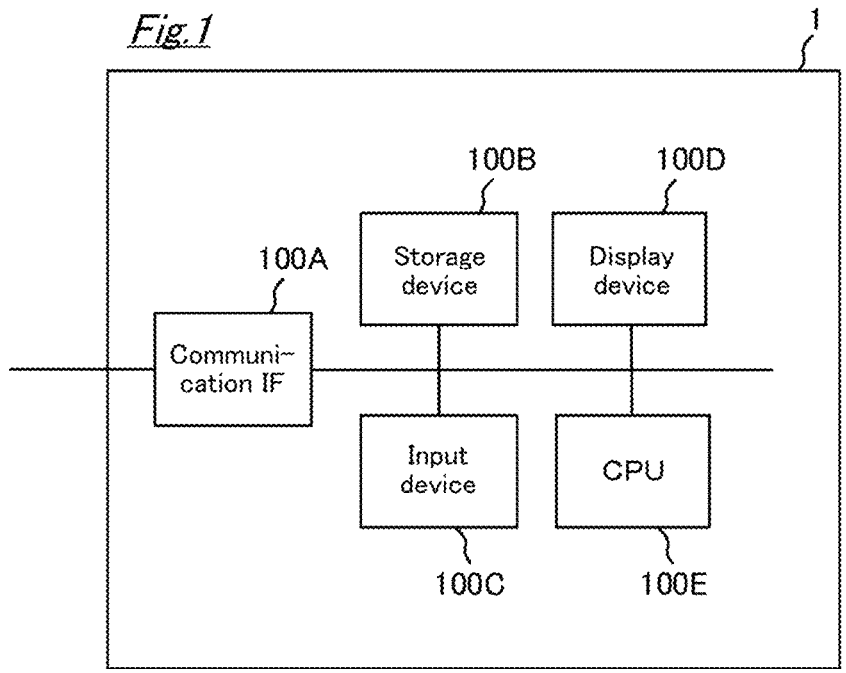
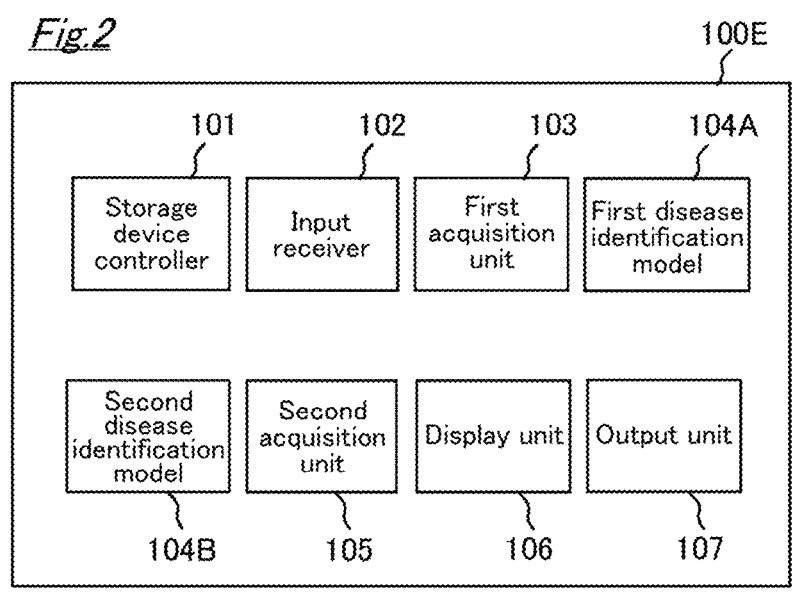

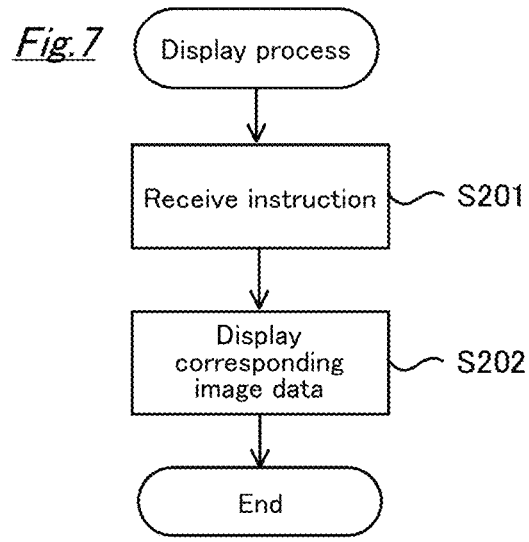
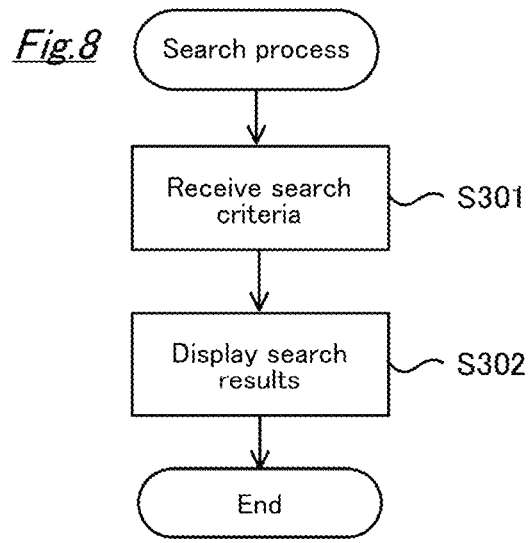

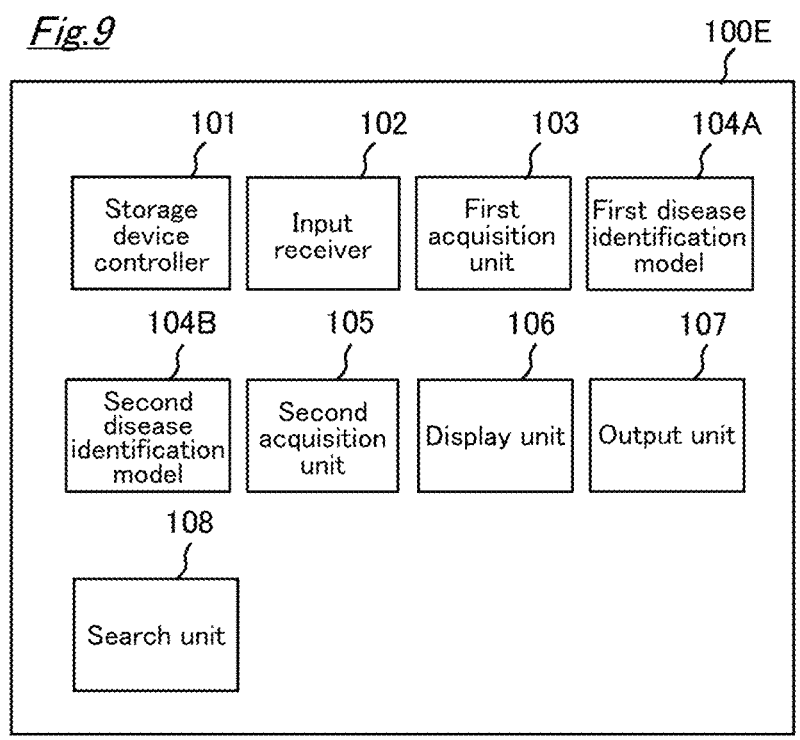

Fig.10

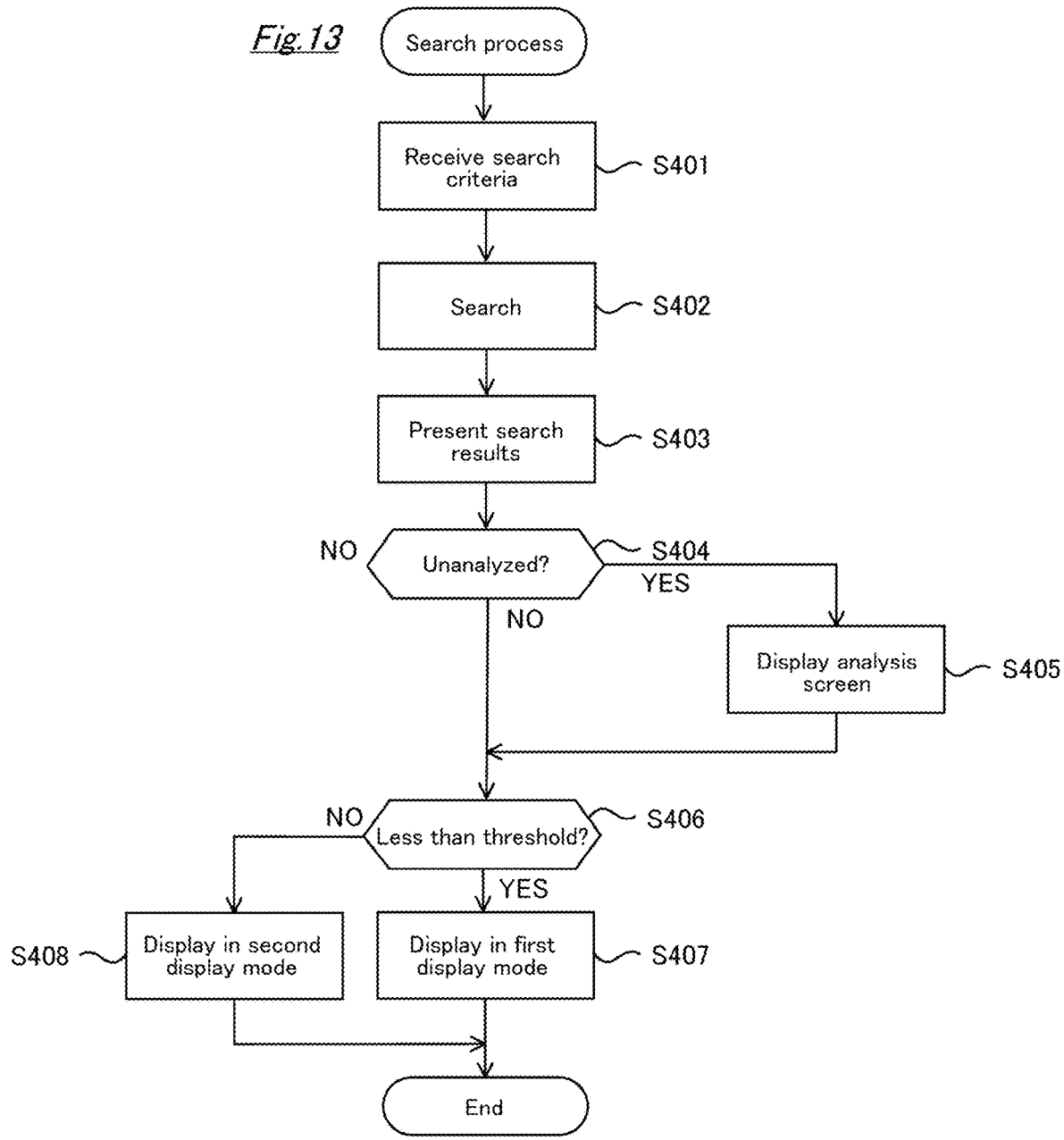

INFORMATION PROCESSING APPARATUS, INFORMATION PROCESSING METHOD, INFORMATION PROCESSING PROGRAM, AND INFORMATION PROCESSING SYSTEM

RELATED APPLICATIONS

The present application is a continuation application of PCT Patent Application No. PCT/JP2022/017558, filed 12 Apr. 2022, which claims priority to Japanese Patent Application No. 2021-073175, filed 23 Apr. 2021. The above referenced applications are hereby incorporated by reference in their entirety.

TECHNICAL FIELD

The present invention relates to an information processing apparatus, an information processing method, an information processing program, and an information processing system.

BACKGROUND ART

There has been disclosed technology of image identification using a learned model (classifier), which employs teaching data in which medical images obtained by photography of a person with a medical imaging apparatus are tagged with some data (see, e.g., Patent Literature 1). This technology employs image identification using a learned model to determine which one of multiple types of lesion patterns is found in a medical image.

PRIOR ART LITERATURE

Patent Literature

JP 2019-33966 A

SUMMARY OF THE INVENTION

Problem(s) to be Solved by the Invention

However, actual medical fields often require quick recognition of patient's severity, symptom, or the like and urgent treatment on the patient. Therefore, not only identification of a medical image, but also how to present an identification result are very important.

The present invention has been made in view of the above drawbacks. It is, therefore, an object of the present invention to provide an information processing apparatus, an information processing method, an information processing program, and an information processing system that facilitates recognition of an identification result.

Means for Solving Problem(s)

In order to solve the above drawbacks, an information processing apparatus according to the present invention has a first acquisition unit configured to acquire measurement data obtained by measurement of a physical condition of a patient, a second acquisition unit configured to acquire, using a first disease identification model generated by machine learning that uses teaching data labeled with first classifications of body portions included in measurement data obtained by measurement of a physical condition of a human and presence of a disease in the body portions, the first classification of a body portion in the measurement data acquired by the first acquisition unit and presence of a disease in the body portion, and a display unit configured to display the presence of the disease in the body portion that is acquired by the second acquisition unit in accordance with the first classification.

Advantageous Effects of the Invention

According to the present invention, there are provided an information processing apparatus, an information processing method, an information processing program, and an information processing system that facilitates recognition of an identification result.

BRIEF DESCRIPTION OF DRAWINGS

FIG. 1 is a diagram showing an example of a hardware configuration of a server according to an embodiment of the present invention.

FIG. 2 is a diagram showing an example of a functional configuration of a server according to an embodiment of the present invention.

FIG. 7 is a flow chart showing an example of information processing conducted by a server according to an embodiment of the present invention.

FIG. 8 is a flow chart showing an example of information processing conducted by a server according to an embodiment of the present invention.

FIG. 9 is a diagram showing an example of a functional configuration of a server according to Variation 2 of the embodiment of the present invention.

FIG. 10 is a diagram showing an example of a screen displayed on a display device of a server according to Variation 2 of the embodiment of the present invention.

FIG. 13 is a flow chart showing an example of information processing conducted by a server according to Variation 2 of the embodiment of the present invention.

MODE(S) FOR CARRYING OUT THE INVENTION

Figure 3:
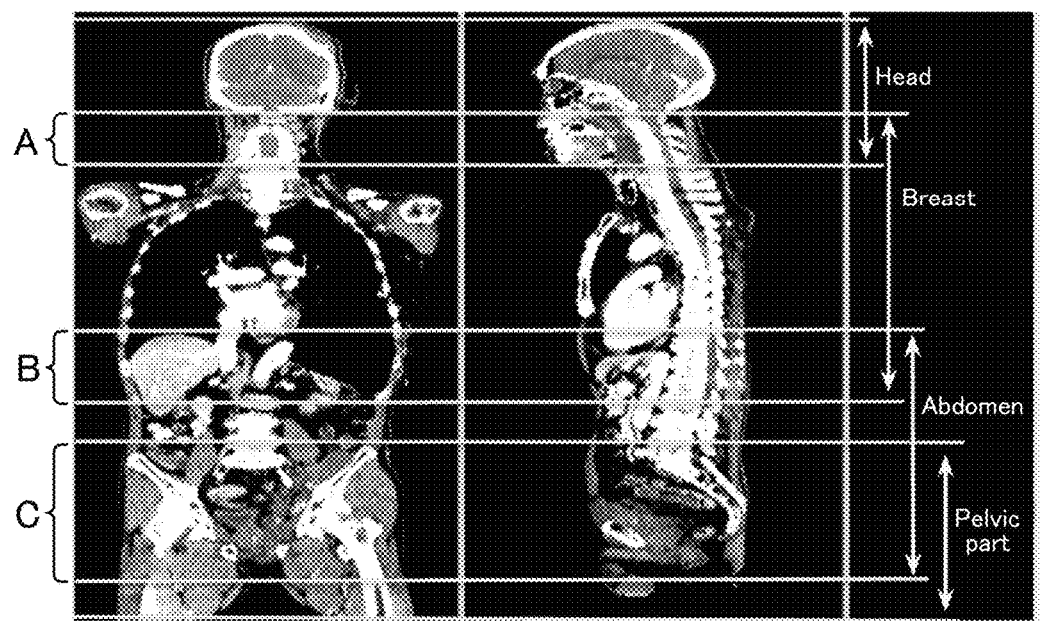
FIG. 3 is a diagram showing an example of classifications according to an embodiment of the present invention.

Embodiments of the present invention will be described below with reference to the drawings. The following description provides an example in which computerized tomography images (CT images) for internal parts of a body of a patient are used as measurement data obtained by measurement of a physical condition of a human. Nevertheless, usable measurement data are not limited to CT images. For example, measurement data may include other medical images such as magnetic resonance imaging (MRI) pictures, three-dimensional measurement data, or other examination data.

In the following embodiments, an information processing apparatus (server) may be implemented as either a stand-alone or on-premises server in which a server is located in a facility or a cloud-based server in which a server is located outside of a facility.

Embodiments

First, a hardware configuration of a server 1 (information processing apparatus) will be described with reference to FIG. 1. As shown in FIG. 1, the server 1 has a configuration in which a communication IF 100A, a storage device 100B, an input device 100C, a display device 100D, and a CPU 100E are connected to each other via a bus (not shown).

The communication IF 100A is a communication interface used when measurement data or teaching data are obtained. The measurement data correspond to image data of a slice of CT images. Metadata, such as identification information (ID), information for management of individual patients (e.g., a patient name, a patient ID, etc.), taken date and time, and a case ID, have been added to the measurement data.

For example, the storage device 100B comprises a hard disk drive (HDD) or a semiconductor memory device (solid state drive (SSD)). Various types of information and information processing programs have been stored in the storage device 100B. The measurement data may be stored in the storage device 100B.

For example, the input device 100C comprises an input device such as a keyboard, a mouse, and a touch panel. The input device 100C may be other devices or equipment as long as it can receive an input. Furthermore, a voice input device may be used for the input device 100C.

For example, the display device 100D comprises a liquid crystal display, a plasma display, an organic EL display, or the like. The display device 100D may be other devices or equipment as long as it can display something (e.g., a cathode ray tube (CRT)).

The CPU 100E controls the server 1 and includes a ROM, a RAM, and the like, which are not shown in the drawings.
(Functions of the Server 1)

Next, functions of the server 1 will be described with reference to FIG. 2. As shown in FIG. 2, the server 1 has functionalities of a storage device controller 101, an input receiver 102, a first acquisition unit 103, a first disease identification model 104A, a second disease identification model 104B, a second acquisition unit 105, a display unit 106, an output unit 107, and the like. The respective functionalities illustrated in FIG. 2 are implemented by the CPU 100E executing an information processing program or the like stored in the ROM or the storage device 100B.

The storage device controller 101 is configured to control the storage device 100B. For example, the storage device controller 101 is configured to write information to the storage device 100B or read information from the storage device 100B.

The input receiver 102 is configured to receive an input operation, for example, from the input device 100C.

The first acquisition unit 103 is configured to acquire measurement data obtained by measurement of a physical condition of a patient via the communication IF 100A. The first acquisition unit 103 may acquire measurement data from other devices connected via a network (e.g., a CT apparatus, a vendor-neutral archive (VNA), or a picture archiving and communication system (PACS), or may acquire measurement data inputted by a user of the server 1 (e.g., a medical worker). When measurement data are stored in the storage device 100B, the first acquisition unit 103 may acquire the measurement data from the storage device 100B. In the present embodiment, the measurement data acquired by the first acquisition unit 103 include a plurality of CT sliced images that can be obtained by taking a region including a plurality of body portions of a patient (for example, a whole body region or a region from a neck to tips of toes of a patient).

The first disease identification model 104A is a model generated by machine learning that uses teaching data labeled with simple classifications of body portions included in measurement data (e.g., locations and names of portions such as a head, a breast, an abdomen, and a pelvic part) and locations and names of diseases in the body portions for each CT slice of image data, which are measurement data on measurement of a physical condition of a human. The first disease identification model 104A is configured to determine presence of any disease in the measurement data with use of the model and determine a severity of each of body portions of a patient and a severity of the whole body of the patient.

The first disease identification model 104A is used to determine that a patient has a severe disease if many sliced images have been found including any disease in measurement data on measurement of a physical condition of the patient, for example, if ten consecutive sliced images have been found including any disease at a head, or the like. For example, the first disease identification model 104A is used to determine that a patient as a whole has a severe disease if the number of portions having a severe disease is equal to or greater than a certain value. A severity may be determined in any manner, and the manner to determine a severity is not limited to the above example.

The first disease identification model 104A is a model (model for extreme emergency) that enables determination of presence of disease and a severity of a body portion (a head, a breast, an abdomen, and a pelvic part (those may be classified in further detailed manner)) at a high speed of about 10 seconds. The first disease identification model 104A is formed of a plurality of models generated by machine learning that uses teaching data. In this embodiment, the first disease identification model 104A is formed of models generated by machine learning that uses teaching data labeled with simple classifications of body portions included in measurement data (e.g., locations and names of portions, such as a head, a breast, an abdomen, and a pelvic part) and locations and names of diseases in the body portions for each CT slice of image data, which are measurement data on measurement of a physical condition of a patient for respective classifications of the body portions. Therefore, the first disease identification model 104A of this embodiment employs models generated for respective classifications of a "head," a "breast," an "abdomen," and a "pelvic part" to determine presence of any disease in the measurement data. The first disease identification model 104A may be formed of a larger number of models.

The second disease identification model 104B is a model generated by machine learning that uses teaching data labeled with detailed classifications of body portions included in measurement data (e.g., locations and names of portions such as a liver, a pancreas, a spleen, a bone, and a blood vessel) and disease locations (for example, specified by a name of a location, segmentation, or a bounding-box (information indicative of a range of an image)) and disease names in the body portions for each CT slice of image data, which are measurement data on measurement of a physical condition of a human. The second disease identification model 104B is a model (model for emergency) that enables determination of body portions classified in further detailed manner than the first disease identification model 104A (a zone of a liver in addition to the name such as a liver, a spleen, or a blood vessel (those portions may be classified in further detailed manner)), a name of a location, segmentation, a bounding-box (information indicative of a range of an image)), a disease name, a severity, and a disease accuracy (probability) within about one minute.

As with the first disease identification model 104A, for example, the second disease identification model 104B is used to determine that a patient has a severe disease if many slices have been found including any disease in measurement data on measurement of a physical condition of the patient, for example, if ten consecutive slices have been found including any disease at a head, or the like. For example, the second disease identification model 104B is used to determine that a patient as a whole has a severe disease if the number of portions having a severe disease is equal to or greater than a certain value.

The determination of a severity with the second disease identification model 104B may include comparing current measurement data (CT slice) with previous measurement data (CT slice) to determine whether the percentage of tissues including a lesion to the whole tissue increases or decreases, weighing with types of diseases (disease names), and the like. A severity may be determined in any manner, and the manner to determine a severity is not limited to the above example.

A user may specify previous measurement data to compare current measurement data with the previous measurement data. Data specifying a patient that are included in the metadata of the measurement data, such as a patient ID, may be used to compare current measurement data with previous measurement data.

In the second disease identification model 104B, information such as a medical plan including a treatment method, a possible medical department to consult, and transfer to an organization of a higher level (hereinafter also referred to as a treatment plan and the like) is associated with names of diseases and severities. Therefore, a determined disease name, a medical plan corresponding to a determined severity, and the like can be displayed.

Thus, the server 1 according to the present embodiment uses the first disease identification model 104A to recognize a simple classification of a body portion (e.g., a head, a breast, an abdomen, and a pelvic part) and determine presence of a disease, a severity, and the like in the simple classification of the body portion at a high speed and then uses the second disease identification model 104B to recognize a detailed classification of a body portion (e.g., a liver, a pancreas, a spleen, a bone, and a blood vessel) and determine, for a disease included in the detailed classification of the body portion, a name and an occurrence location of the disease, occurrence segment information, a severity, a disease accuracy (probability), and the like. Specifically, with use of the first disease identification model 104A as a model for extreme emergency and the second disease identification model 104B as a model for emergency, the first disease identification model 104A enables immediate recognition of a portion of a body where a disease has occurred and a severity (about 10 second to display (render) the information on the display device 100D), and the second disease identification model 104B enables recognition of information such as a name and an occurrence location of the disease (hereinafter also referred to as details of a disease) and a severity for each of detailed portions (one minute to display (render) the information).

In the present embodiment, information on respective diseases and portions are polygonised for CT sliced images to generate teaching data to be labeled. (Polygonization has been well known in the art and is not described herein.) The teaching data enable recognition of a location, a name, and a size of a disease. The segment information refers to inputted polygons having interiors painted with colors for respective disease names.

In the present embodiment, data generated by polygonising information on respective diseases and portions for CT sliced image are used for teaching data. However, any teaching data generated by other techniques may be used as long as the teaching data enable determination of a body portion (a zone of a liver in addition to the name such as a liver, a spleen, or a blood vessel (those portions may be classified in further detailed manner)), a name of a portion, segmentation, a bounding-box (information indicative of a range of an image), a disease name, and a severity.

The output unit 107 is configured to output some or all of information acquired by at least one of the first acquisition unit 103 and the second acquisition unit 105. More specifically, the output unit 107 is configured to output PDF files with diagnostic imaging reports or data files for statistical analysis for a research application that are generated from information acquired by at least one of the first acquisition unit 103 and the second acquisition unit 105. The data files are JavaScript (registered trademark) object notation (json) files or comma separated values (csv) files including metadata of patient information included in identification results (including a severity) of each of the first disease identification model 104A and the second disease identification model 104B or input measurement data. The information that can be downloaded (outputted) is not limited to the above example and may include other information that can be obtained from the server 1. The data files may be outputted (downloaded) in any file format, for example, a file format other than json or csv.

FIG. 3 is a diagram showing an example of simple classifications of body portions (a head, a breast, an abdomen, and a pelvic part) according to an embodiment of the present invention. The classifications are labelled by anatomical classifications of body portions. As shown in FIG. 3, body portions are classified with a "head," a "breast," an "abdomen," and a "pelvic part" in the present embodiment, and the teaching data are labeled with those classifications.

When body portions are classified in a "head," a "breast," an "abdomen," and a "pelvic part," some CT slices of image data include both of a "head" and a "breast" (overlap region A), both of a "breast" and an "abdomen" (overlap region B), or both of an "abdomen" and a "pelvic part" (overlap region C) as illustrated in FIG. 3.

In the present embodiment, the first disease identification model 104A and the second disease identification model 104B are stored in the storage device 100B of the server 1. Nevertheless, the first disease identification model 104A and the second disease identification model 104B do not necessarily need to be stored in the storage device 100B. Furthermore, some or all of various kinds of information stored in the storage device 100B may be stored in an external storage device, such as a universal serial bus (USB) memory or an external HDD, or a storage device of another information processing apparatus connected via a local network. In this case, the server 1 retrieves or acquires various kinds of information stored in the external storage device or the storage device of the other information processing apparatus.

The second acquisition unit 105 is configured to acquire, with use of the first disease identification model 104A, information generated by the first disease identification model 104A, such as classifications of body portions (a head, a breast, an abdomen, and a pelvic part) in measurement data acquired by the first acquisition unit 103, and presence and a severity of a disease (hereinafter also referred to as a first identification result).

Furthermore, the second acquisition unit 105 is configured to acquire, with the second disease identification model 104B, information generated by the second disease identification model 104B, such as a name and an occurrence location of a disease included in the measurement data acquired by the first acquisition unit 103, occurrence segment information, a severity (details of the disease) (hereinafter also referred to as a second identification result). The second acquisition unit 105 is also configured to acquire, with the second disease identification model 104B, an identified disease name, a treatment plan corresponding to an identified severity, and the like.

The display unit 106 is configured to display information such as measurement data acquired by the first acquisition unit 103 (CT sliced images), first and second identification results acquired by the second acquisition unit 105, and a treatment plan on the display device 100D.

When the input receiver 102 receives display instructions for measurement data on measurement of a physical condition of a patient, the display unit 106 is also configured to display the measurement data on the measurement of the physical condition of the patient, which have been acquired by the first acquisition unit 103, in accordance with the display instructions received by the input receiver 102.

The display unit 106 is also configured to display the identification results acquired by the second acquisition unit 105 in a manner corresponding to those identification results (for example, with different colors or different fill patterns depending on a severity of a disease).

Details of display on the display device 100D by the display unit 106 will be described later with reference to FIG. 4.

Figure 4:
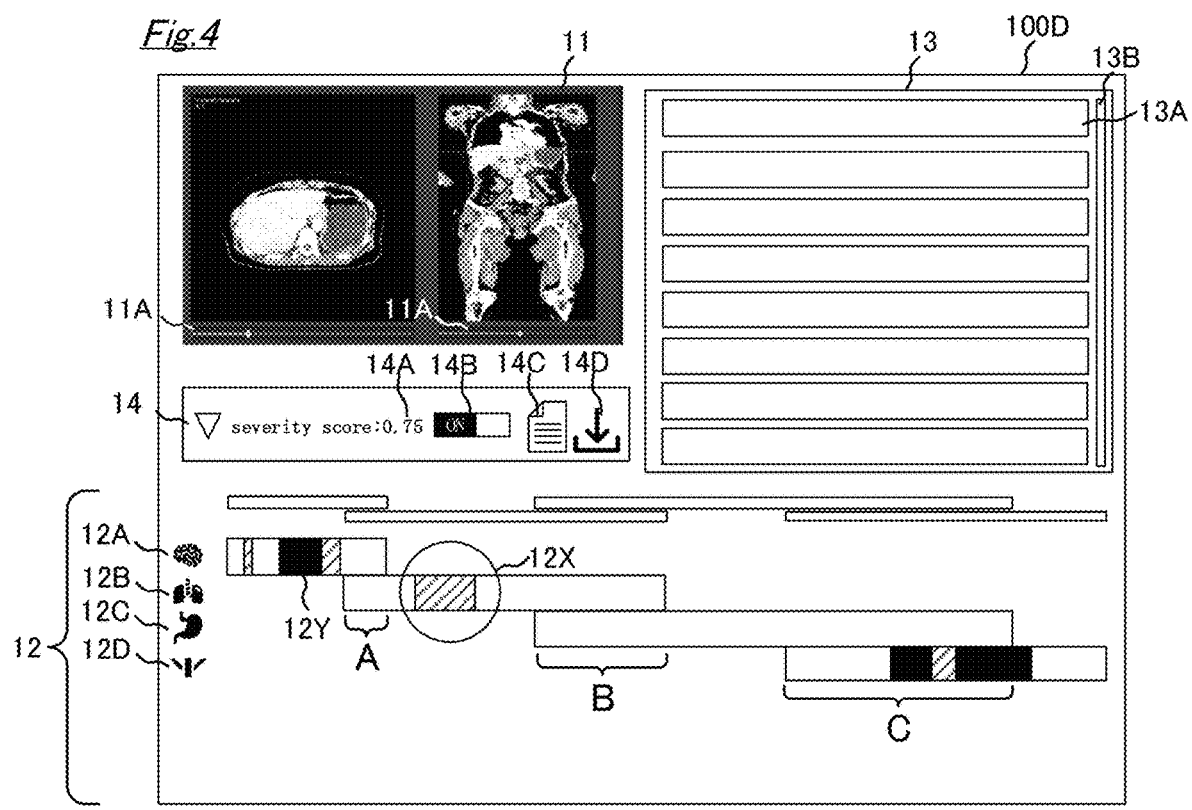
FIG. 4 is a diagram showing an example of a screen displayed on a display device of a server according to an embodiment of the present invention.
Figure 5:
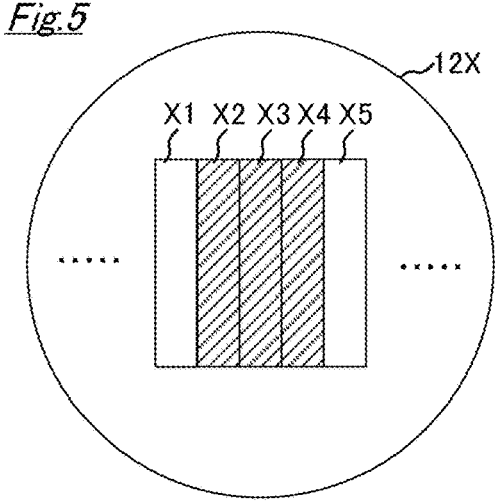
FIG. 5 is a diagram showing an example of a screen displayed on a display device of a server according to an embodiment of the present invention.

FIGS. 4-5 are diagrams showing examples of a screen displayed on the display device 100D of the server 1.

FIG. 4 is a screen illustrating an example of information displayed on the display device 100D by the display unit 106 of the server 1.

As shown in FIG. 4, the display unit 106 is operable to display measurement data (image data) acquired by the first acquisition unit 103 in a first display area 11 as a viewer component, an identification result from the first disease identification model 104A that is acquired by the second acquisition unit 105 in a second display area 12 as a timeline component, an identification result from the second disease identification model 104B that is acquired by the second acquisition unit 105 in a third display area 13 as an information component, and a severity of an entire patient or icons for other operations in a fourth display area 14 as a meta component.

The respective display areas will be described below.

In the first display area 11, there are displayed measurement data acquired by the first acquisition unit 103 (so-called CT sliced images). No identification results (processing results) by the first disease identification model 104A and the second disease identification model 104B, which are AI models, are included in the first display area 11. For example, one CT sliced image included in a plurality of CT sliced images acquired by the first acquisition unit 103 (CT images of a whole body) is displayed in the first display area 11. Images displayed in the first display area 11 are not limited to this example. An image to which a plurality of CT sliced images acquired by the first acquisition unit 103 have been reorganized (for example, an image in which an axial direction of the cross section has been changed by 90 degrees) may be displayed the first display area 11. Furthermore, an image generated by processing CT sliced images acquired by the first acquisition unit 103 depending on an identification result from at least one of the first disease identification model 104A and the second disease identification model 104B may be displayed the first display area 11. For example, the processing includes filling respective areas in a CT sliced image with different colors or patterns depending on presence of a disease in those areas, a type of a disease, or a severity of a disease. A user can use a slider 11A to vary measurement data from a head to feet in a three-dimensional direction within the first display area 11 and can change a brightness of the screen such that bones become more visible or a lung field becomes more visible (windowing). When the user clicks the rendered image, a return value of radiation at the clicked point may be displayed (and used to analyze details of a disease). Specifically, the server 1 is configured to change a CT sliced image displayed in the first display area 11 among a plurality of CT sliced images acquired by the first acquisition unit 103 in response to a user's operation to the slider 11A. Furthermore, the server 1 is configured to change parameters relating to a CT sliced image displayed in the first display area 11 and display information on the CT image slice in response to a user's operation to a predetermined area of the first display area 11.

In the second display area 12, there are displayed identification results from the first disease identification model 104A that have been acquired by the second acquisition unit 105. (The identification results are rendered in about 10 seconds after taken CT images have been inputted.) As shown in FIG. 4, the display unit 106 is configured to display identification results for each of the classifications of the body portions in a belt-shaped manner corresponding to the identification results (for example, with different colors or fill patterns depending on a severity of a disease). In the example illustrated in the second display area 12 of FIG. 4, the "white portion" means "no disease," the "hatched portion" means "mild disease," and the "black portion" means "severe disease." However, the manner in which the identification results are displayed can be selected as desired and is not limited to the example illustrated in the second display area 12 of FIG. 4. In this manner, when the strip in each of the rows are displayed with different colors (blue, yellow, red, etc.) or different fill patterns, the user can recognize where and how many diseases have been found at a glance. For example, in the example of FIG. 4, identification results of severities for a plurality of CT sliced images acquired by the first acquisition unit 103 are displayed side by side so as to correspond to locations where those sliced images were taken. Specifically, the identification result for a CT sliced image taken near the head of the patient is displayed on the left side of the screen. The identification result for a CT sliced image taken near the feet of the patient is displayed on the right side of the screen. Therefore, a user can readily recognize which body portion of the patient suffers from a severe disease based on a horizontal location of a region having a color corresponding to the "severe disease" in each of the strips. Furthermore, since the strips are separately displayed for the respective classifications of the body portions, a user can readily recognize a severity for each of the body portions and can determine a treatment plan in a short period of time.

When body portions are classified in a "head," a "breast," an "abdomen," and a "pelvic part," some of image data include both of a "head" and a "breast," both of a "breast" and an "abdomen," or both of an "abdomen" and a "pelvic part" as described in connection with FIG. 3. Therefore, portions of the strips corresponding to the respective body portions are located in an overlapped manner in the horizontal direction of the screen. In the overlapped portions, one piece of image data includes both of a "head" and a "breast," both of a "breast" and an "abdomen," or both of an "abdomen" and a "pelvic part." (The overlap regions A, B, and C illustrated in FIG. 4 correspond to the overlap regions A, B, and C illustrated in FIG. 3.)

Accordingly, in the overlap region A where the image data include both of a "head" and a "breast," the identification results from the disease identification model for a "head" and the disease identification model for a "breast" are displayed.

In the overlap region B where the image data include both of a "breast" and an "abdomen," the identification results from the disease identification model for a "breast" and the disease identification model for an "abdomen" are displayed.

In the overlap region C where the image data include both of an "abdomen" and a "pelvic part," the identification results from the disease identification model for an "abdomen" and the disease identification model for a "pelvic part" are displayed. For example, in the overlap region C, no color has been added to the strip corresponding to the "abdomen" while the strip corresponding to the "pelvic part" has been colored with "severe disease" or "mild disease." This indicates that "no disease" has been identified by the disease identification model for the "abdomen" but that a "disease" has been identified by the disease identification model for the "pelvic part" in one CT sliced image included in the overlap region C.

In FIG. 4, the disease levels are displayed in the order of the "head 12A," the "breast 12B," the "abdomen 12C," and the "pelvic part 12D." Such an order corresponds to locations of respective body portions of a patient in the vertical direction. Therefore, this order is advantageous in that a user can intuitively understand the disease levels. However, the disease levels do not necessarily need to be in the order of the "head 12A," the "breast 12B," the "abdomen 12C," and the "pelvic part 12D." The order in which the "head 12A," the "breast 12B," the "abdomen 12C," and the "pelvic part 12D" are displayed can be selected as desired. For example, as described later, if the number of rows of the strips increases, confirmation of those strips may take more time. In such a case, the display unit 106 may sort the strips corresponding to the respective body portions according to severities of the respective body portions, which have been acquired from the first disease identification model 104A, so that the strips corresponding to the respective body portions are displayed from the top in the descending order of severities. This sorted display allows a user to set a higher priority to a more dangerous portion to confirm a symptom or the like. The display order of the strips is not limited to the above example (severity order). For example, the strips may be sorted and displayed in an order corresponding to body portions, or only the strips for an external injury or an internal disease may be displayed. Thus, the strips may be sorted and displayed in various manners. A user may specify how to sort the strips.

As described above, simple classifications of body portions include a head, a breast, an abdomen, and a pelvic part in the present embodiment. For example, if the "breast" is subdivided into a "breast external injury" and a "breast internal disease" to provide multilayered classifications, the classifications 12A-12D illustrated in FIG. 4 are also displayed in a multilayered manner. In other words, the screen illustrated in FIG. 4 is provided by way of example of the embodiment. When the classifications of body portions are multilayered, the multilayered classifications are displayed in the second display area 12 of the display device 100D. Multilayered classifications include various patterns: For example, each of the classifications of the head, the breast, and the abdomen may be subdivided into an external injury and an internal disease. The classification of the abdomen may be subdivided into a liver and a stomach. The classification of the breast may be subdivided into a heart and lungs. The subdivision is not limited to the above examples. In another pattern, a row strip for a specific disease, such as presence of a COVID disease in a lung field, may be added. Thus, although the second display area 12 of FIG. 4 has a strip arrangement of four rows of a head, a breast, an abdomen, and a pelvic part, the number of rows (bands) displayed in the second display area 12 of FIG. 4 varies according to the number of extreme emergency models corresponding to the subdivided levels.

FIG. 5 is a partial enlarged view of a region 12X in the second display area 12 illustrated in FIG. 4. The identification results for the "head 12A," the "breast 12B," the "abdomen 12C," and the "pelvic part 12D" as displayed on the display device 100D are aggregates of identification results for each one of a plurality of pieces of measurement data (image data) acquired by the first acquisition unit 103. Therefore, as shown in FIG. 5, the corresponding number of identification results to the number of pieces of measurement data (image data) are displayed. In the example illustrated in FIG. 5, each of identification results X1-X5 corresponds to one piece of measurement data (one CT slice of image data). When a user selects an identification result to be displayed from the identification results X1-X5 illustrated in FIG. 5 with use of a pointing device (input device 100C) such as a mouse, then measurement data (a CT slice of image data) is displayed on the screen of FIG. 4. Specifically, the server 1 switches a CT sliced image displayed in the first display area 11 among a plurality of CT sliced images acquired by the first acquisition unit 103 in response to a user's operation to the second display area 12. For example, when the black portion of the strip for the head is clicked in the second display area 12 illustrated in FIG. 4, then an image of measurement data in which the head disease has been found can be confirmed in the first display area 11 (viewer component), which results in great convenience.

In the third display area 13, there are displayed identification results (including treatment plans or the like) from the second disease identification model 104B that have been acquired by the second acquisition unit 105 (those results are rendered within about one minute after input of taken CT images). In the third display area 13, there are displayed comments (natural language) that convey a body portion and a location of that body portion where a disease has been found, a type of the disease, and a severity of the disease, such as "damage to blood vessels at the right middle lobe of lung, active bleeding," and an ID (e.g., slice number) of the corresponding piece of measurement data. The display unit 106 is configured to display the aforementioned identification results for diseases (comments and IDs of measurement data). The display unit 106 is also configured to join a display frame 13A to a lower portion of the screen depending on the number of diseases found in the measurement data so as to display identification results for the diseases found in the measurement data.

If the number of the display frames 13A increases, confirmation of those display frames may take more time as in the second display area 12 (timeline component). In this case, the display unit 106 may sort the display frames 13A according to severities acquired from the second disease identification model 104B so that the display frames are displayed from the top in the descending order of severities. This sorted display allows a user to set a higher priority to a more dangerous portion to confirm a symptom or the like. The display order of the strips is not limited to the above example (severity order). For example, as in the second display area 12 (timeline component), the display frames may be sorted and displayed in an order corresponding to body portions, or only the display frames for an external injury or an internal disease may be displayed. Thus, the display frames may be sorted and displayed in various manners. A user may specify how to sort the display frames.

Because a user may often want to know presence of a specific disease, a search window may be provided at the upper right portion of the third display area 13 (information component). When a user inputs a disease name or a body portion name in the search window, display frames 13A (cards) corresponding to the inputted name may be displayed.

In the fourth display area 14, a severity 14A of the entire patient (whole body) is displayed. The severity of the entire patient is a value (score) derived comprehensively in consideration of identification results from disease identification models (the first disease identification model 104A and the second disease identification model 104B in the present embodiment) for a plurality of CT sliced images acquired by the first acquisition unit 103. Use of this value enables comparison of levels of severe diseases of a plurality of patients and comparison of measurement data for the same patient that were taken on different dates. The value (score) derived comprehensively in consideration of identification results from a disease identification model may be calculated in any manner. For example, a heavier weight may be attached to an identification result of the second disease identification model 104B from which a disease is to be identified in a more detailed manner.

Furthermore, a user can perform an ON/OFF operation on an ON/OFF button 14B to determine whether or not the identification results are displayed (rendered). When the ON/OFF button 14B is turned ON, the display unit 106 displays (renders) disease segment information and a disease name of an identification result from the second disease identification model 104B on the screen (viewer) when the measurement data (a CT sliced image or the like) are displayed in the first display area 11 (viewer component). When the ON/OFF button 14B is turned OFF, the display unit 106 does not display (render) disease segment information or a disease name of an identification result from the second disease identification model 104B on the screen (viewer) (non-display). The display unit 106 may add an ON/OFF button that allows a user to determine whether or not to display (render) an identification result from the first disease identification model 104A on the screen (viewer), in the screen illustrated in FIG. 4.

There may be a need for efficiently viewing any identification results on the screen (viewer) and a need for viewing an image itself in detail without such identification results. Therefore, provision of the ON/OFF button 14B offers added convenience.

Furthermore, a user may operate an icon 14C to convert the overall identification results, which incorporate results from the first disease identification model 104A and results from the second disease identification model 104B, into a PDF file, which conforms to the format of diagnostic imaging reports that have been familiar to medical doctors, and to display the converted PDF file. Conversion to a PDF file, which conforms to the format of diagnostic imaging reports that have been familiar to medical doctors, enables the PDF file to be stored on electronic charts in the same manner as reports created by other users and makes it easier to deliver the results to a medical doctor who does not use the application directly. Thus, greater convenience is provided.

A user may operate a download icon 14D to download (output) the overall identification results, which incorporate results from the first disease identification model 104A and results from the second disease identification model 104B. For example, the information to be downloaded includes a PDF file that conforms to the format of diagnostic imaging reports displayed by operation of the icon 14C and a data file for statistical analysis for a research application. The data file is a json file or a csv file including metadata of patient information included in respective identification results (including a severity) from the first disease identification model 104A and the second disease identification model 104B or input measurement data. The information that can be downloaded (outputted) is not limited to the above example. The information that can be downloaded (outputted) may include other type of information that can be acquired from the server 1.

(Information Processing)

Figure 6:
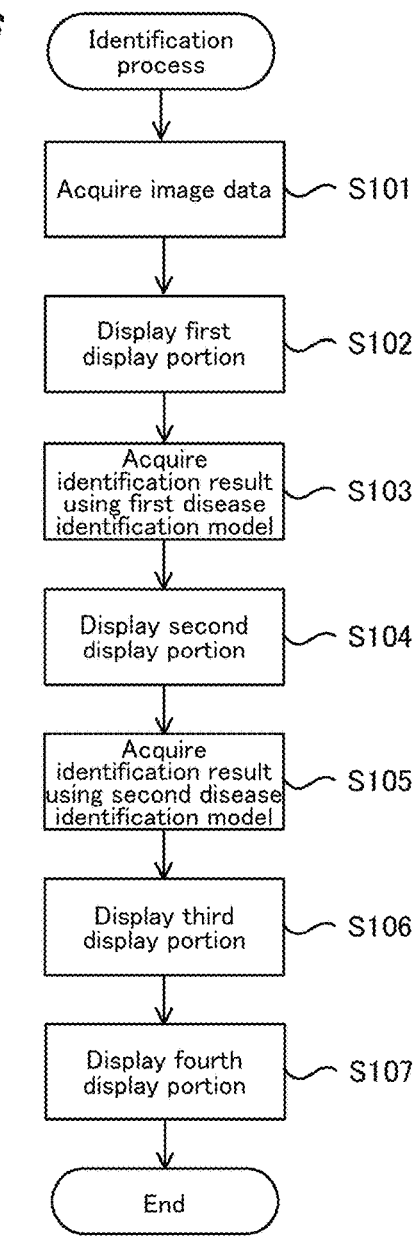
FIG. 6 is a flow chart showing an example of information processing conducted by a server according to an embodiment of the present invention.

FIGS. 6-8 are flow charts showing an example of identification information processing of the server 1. The information processing of the server 1 will be described below with reference to FIGS. 6-8. In the following description, the same components as described in connection with FIGS. 1-5 are denoted by the same reference numerals and will not be described below repetitively.

(Information Processing)

FIG. 6 is a flow chart showing an example of an identification process of the server 1. The identification process of the server 1 will be described below with reference to FIG. 6.

(Step S101)

When an input of CT images (measurement data) taken for internal parts of a body of a patient is received, the first acquisition unit 103 of the server 1 acquires measurement data obtained by measurement of a physical condition of the patient to be examined.

(Step S102)

When the first acquisition unit 103 of the server 1 acquires the measurement data, the display unit 106 displays (renders) the measurement data (image data) acquired by the first acquisition unit 103 in the first display area 11 of FIG. 4, so that the measurement data (CT sliced images) are visible (in a viewing mode). The first acquisition unit 103 may acquire measurement data from another device connected via a network (for example, a CT device, a vendor-neutral archive (VNA), or a picture archiving and communication system (PACS)) or may acquire measurement data inputted by a user of the server 1.

(Step S103)

The second acquisition unit 105 of the server 1 acquires information generated by the first disease identification model 104A (first identification result), such as classifications of body portions in the measurement data acquired by the first acquisition unit 103 (a head, a breast, an abdomen, and a pelvic part), presence of any disease, and a severity of the disease, with use of the first disease identification model 104A.

(Step S104)

The display unit 106 of the server 1 displays (renders) the information acquired by the second acquisition unit 105 in the second display area 12. With the process of Step S104 (rendering), the information described in connection with FIG. 4 is displayed in the second display area 12. In the present embodiment, the rendering time is about 10 seconds. The rendering time varies according to performance of a computer (server 1) and a level of detail of the classifications. Thus, a user can recognize where and how many diseases have been found at a glance. As described above, when the second display area 12 is displayed (rendered), the respective strips may be sorted according to severities so that the strips are displayed from the top in the descending order of severities. Alternatively, the strips may be sorted and displayed in an order corresponding to body portions, or only the strips for an external injury or an internal disease may be displayed. Thus, the strips may be sorted and displayed in various manners. Furthermore, the strips may be sorted in the order specified by a user.

(Step S105)

The second acquisition unit 105 acquires information generated by the second disease identification model 104B (second identification result), such as a name of a disease included in the measurement data acquired by the first acquisition unit 103, an occurrence location of the disease, occurrence segment information, and a severity of the disease, with use of the second disease identification model 104B. The second acquisition unit 105 also acquires a name of the identified disease, a treatment plan corresponding to the severity, and the like with use of the second disease identification model 104B.

(Step S106)

The display unit 106 of the server 1 displays (renders) the information acquired by the second acquisition unit 105 in the third display area 13. With the process of Step S106 (rendering), the information described in connection with FIG. 4 is displayed in the third display area 13. In the present embodiment, the rendering time is about one minute. The rendering time varies according to performance of a computer (server 1) and a level of detail of the classifications. Thus, a user can recognize a name of a disease for each of the detailed classifications of the body portions, information on an occurrence location of the disease, a treatment plan, and the like. As described above, when the third display area 13 is displayed (rendered), the respective strips may be sorted according to severities so that the strips are displayed from the top in the descending order of severities. Alternatively, the strips may be sorted and displayed in an order corresponding to body portions, or only the strips for an external injury or an internal disease may be displayed. Thus, the strips may be sorted and displayed in various manners. Furthermore, the strips may be sorted in the order specified by a user.

(Step S107)

The display unit 106 of the server 1 displays a severity for each of patients (for patient comparison) in the fourth display area 14.

As described in connection with FIG. 4, when the ON/OFF button 14B in the fourth display area 14 is OFF, the display unit 106 does not display any identification result from the second disease identification model 104B on the screen (viewer). There is provided another ON/OFF button that allows a user to determine whether or not to display (render) an identification result from the first disease identification model 104A on the screen (viewer) (display/non-display). When this ON/OFF button is OFF, the display unit 106 does not display (render) any identification result from the first disease identification model 104A on the screen (viewer).

In the above description, the display unit 1060 performs displaying (rendering) in the order of the first display area 11 (viewer component), the second display area 12 (timeline component), the third display area 13 (information component), and the fourth display area 14 (meta component). However, internal processing for the displaying does not necessarily need to be conducted in the aforementioned order of the first display area 11 to the fourth display area 14. For example, some of the processing may be conducted in parallel. (Nevertheless, it is preferable that the identification process of the first disease identification model 104A for extreme emergency is not performed at a later stage.)

(Display Process)

FIG. 7 is a flow chart showing an example of a display process of the server 1. An example of a display process of the server 1 will be described with reference to FIG. 7.

(Step S201)

The input receiver 102 of the server 1 receives an instruction to display measurement data on measurement of a physical condition of a patient.

(Step S202)

When the input receiver 102 receives the instruction to display measurement data on measurement of a physical condition of a patient, then the display unit 106 of the server 1 displays an image described with reference to FIG. 5 on the display device 100D in accordance with the instruction received by the input receiver 102. Specifically, when the input receiver 102 receives the instruction to display measurement data on measurement of a physical condition of a patient, then the display unit 106 of the server 1 displays measurement data (image data) corresponding to the instruction received by the input receiver 102 among measurement data on measurement of the physical condition of the patient that has been acquired by the first acquisition unit 103.

(Search Process)

FIG. 8 is a flow chart showing an example of a search process of the server 1. An example of a search process of the server 1 will be described with reference to FIG. 8.

(Step S301)

The input receiver 102 of the server 1 receives search criteria, such as a disease name or a body portion name.

(Step S202)

When the input receiver 102 receives the search criteria, then the display unit 106 of the server 1 displays a display frame 13A (card) that matches the search criteria received by the input receiver 102 in the third display area 13. Specifically, the display unit 106 of the server 1 displays a display frame 13A (card) that includes the disease name or the body portion name included in the search criteria in the third display area 13.

As described above, a server 1 according to an embodiment has a first acquisition unit 103 configured to acquire measurement data obtained by measurement of a physical condition of a patient, a second acquisition unit 105 configured to acquire, using a first disease identification model 104A generated by machine learning that uses teaching data labeled with first classifications of body portions included in measurement data obtained by measurement of a physical condition of a human, the first classification of a body portion in the measurement data acquired by the first acquisition unit 103 and presence of a disease in the body portion, and a display unit 106 configured to display the presence of the disease in the body portion that is acquired by the second acquisition unit 105 in accordance with the first classification.

Accordingly, presence of a disease can be confirmed at a body portion in accordance with the classification, resulting in greater convenience.

The first disease identification model 104A of the server 1 according to an embodiment is configured to identify a severity of each of the body portions of the patient based on presence of the disease of the body portion. The second acquisition unit 105 is configured to acquire a severity of each of the body portions of the patient that is identified by the first disease identification model 104. The display unit 106 is configured to display a severity for each of the body portions that is acquired by the second acquisition unit 105 in a manner that corresponds to the severity.

Accordingly, a severity of a patient can readily be recognized, resulting in greater convenience.

The second acquisition unit 105 of the server 1 according to this embodiment is configured to acquire, with use of a second disease identification model 104B generated by machine learning that uses teaching data labeled with second classifications of body portions included in measurement data, which are more detailed classifications than the first classifications, and presence of diseases in body portions, for measurement data on measurement of a physical condition of a human, classifications of and details of diseases in body portions of measurement data acquired by the first acquisition unit 103. The display unit 106 of the server 1 displays the details of diseases for each of the body portions that have been acquired by the second acquisition unit 105.

In this manner, details of diseases (as illustrated in the third display area 13 of FIG. 4) can be confirmed in addition to information acquired by the first disease identification model 104A (as illustrated in the second display area 12 of FIG. 4), resulting in greater convenience.

The display unit 106 of the server 1 according to the present embodiment is configured to display information acquired from the first disease identification model 104A and the second disease identification model 104B by the second acquisition unit 105 in an order of certain priority, for example, in order of severities or body portions, with only external injuries or with only internal diseases, in an order specified by a user, or the like.

Therefore, when the information is sorted according to severities and displayed from the top in the descending order of severities, a user can set a higher priority to a more dangerous portion to confirm a symptom or the like, resulting in greater convenience.

The measurement data of this embodiment are measurement data obtained by scanning a body of a patient. The display unit 106 of the server 1 of this embodiment is configured to display presence of diseases in body portions that have been acquired by the second acquisition unit 105 according to the scanning order.

Thus, identification results for measurement data obtained by computed tomograph (CT) or magnetic resonance imaging (MRI) are displayed in the order (same order) in which they were obtained. Therefore, a user can readily recognize the relationship between identification results and locations of a patient from which measurement data were obtained, resulting in greater convenience.

The server 1 of this embodiment has an input receiver 102 (first receiver) configured to receive a display instruction to display measurement data on measurement of a physical condition of a patient. The display unit 106 is configured to display measurement data on measurement of a physical condition of a patient that have been acquired by the first acquisition unit 103 in response to contents received by the input receiver 102.

Accordingly, when a user would like to examine a specific portion, the original measurement data can readily be confirmed, resulting in greater convenience.

The server 1 according to this embodiment has an input receiver 102 (second receiver) configured to receive an instruction for the display unit 106 to display or not to display information acquired by the second acquisition unit. The display unit 106 is configured to display or not to display information acquired by the second acquisition unit 105 in response to contents received by the input receiver 102.

Accordingly, information acquired by the second acquisition unit 105 is allowed to be displayed or not to be displayed as needed, resulting in greater convenience.

The server 1 of this embodiment has an output unit 107 configured to output some or all of information acquired by the second acquisition unit 105.

Thus, some or all of information acquired by the second acquisition unit 105 can be outputted and obtained as needed, resulting in greater convenience.

Variation 1 of the Embodiment

In the above embodiment, identification using the first disease identification model 104A and the second disease identification model 104B is made for measurement data on measurement of a physical condition of a human for confirmation. In a case where the first disease identification model 104A can have a sufficiently high identification precision, or in a case of emergency, identification using the second disease identification model 104B may be made only for measurement data that have produced an identification result in which any disease has been found with use of the first disease identification model 104A.

A user may operate the input device 100C to specify a body portion, a location, a region, or the like that is to be subjected to identification using the second disease identification model 104B. Furthermore, a user may operate the input device 100C to specify a priority of a body portion, a location, a region, or the like that is to be subjected to identification using the second disease identification model 104B. This configuration enables details of a portion requiring an emergency treatment to be identified preferentially, resulting in greater convenience.

In the above embodiment, the simple classifications of body portions include a head, a breast, an abdomen, and a pelvic part, and the detailed classifications of body portions include a liver, a pancreas, a spleen, a bone, and a blood vessel. Nevertheless, body portions may be classified in any manner. The manner to classify body portions is not necessarily limited to the examples presented in the above embodiment. For example, the "breast" may be subdivided into a "breast external injury" and a "breast internal disease." Thus, body portions may be classified not only with a level of the name of the body portions, but also with types of diseases.

It is sufficient to diagnose a condition of a patient with use of the first disease identification model 104A, which is a model for extreme emergency, in about 10 seconds, and then diagnose a detailed condition of the patient with use of the second disease identification model 104B, which is a model for emergency. For example, while the first disease identification model 104A defines body portions by a "head," a "breast," an "abdomen," and a "pelvic part," it may use more detailed classifications of body portions. This holds true for the second disease identification model 104B.

The above embodiment performs two-stage diagnosis using the first disease identification model 104A, which is a model for extreme emergency, and the second disease identification model 104B, which is a model for emergency. Nevertheless, three or more stages of diagnosis may be implemented with a first disease identification model, a second disease identification model, a third disease identification model, and the like.

The server 1 may be implemented by any device other than a server computer, such as a general purpose computer, a dedicated computer. or a portable terminal, or any combination of two or more of those devices (e.g., a system). When the server 1 is formed by a combination of a plurality of devices, those devices may communicate with each other via a network such as a WAN or a LAN. The network may use wireless communication or wired communication, or a combination of wireless communication and wired communication.

Variation 2 of the Embodiment

FIG. 9 is a diagram showing an example of a functional configuration of the server 1 according to Variation 2 of the embodiment. As shown in FIG. 9, the server 1 has functionalities of a storage device controller 101, an input receiver 102, a first acquisition unit 103, a first disease identification model 104A, a second disease identification model 104B, a second acquisition unit 105, a display unit 106, an output unit 107, a search unit 108, and the like. The functional configuration of the server 1 according to Variation 2 of the embodiment will be described below with reference to FIG. 9. Functional configurations that differ from the functional configurations described with reference to FIG. 2 will be described.

The input receiver 102 is configured to receive search criteria, such as taken time (e.g., year and date, or beginning year and date to ending year and date) or a patient name (which may be a patient ID). The search criteria may include a plurality of patient names (two or more patient names).

The input receiver 102 is also configured to receive a display size of information acquired by the first acquisition unit 105.

The first acquisition unit 103 is configured to acquire measurement data retrieved by the search unit 108, which will be described later.

The display unit 106 is configured to display search results by the search unit 108. The display unit 106 is also configured to display information acquired by the second acquisition unit in different manners depending on the display size received by the input receiver 102, specifically on whether or not the display size received by the input receiver 102 is less than a threshold. The display unit 106 uses a predefined threshold (preset value). The threshold can preferably be changed by a user. The threshold may be determined depending on the size or resolution of the display device 100D. The display with the display unit 106 will be described with reference to FIGS. 10 to 12.

The search unit 108 is configured to retrieve measurement data that meet the search criteria received by the input receiver 102. For example, if taken time is specified in the search criteria, the search unit 108 retrieves measurement data in a range specified by the search criteria. For example, if a patient name or a patient ID is specified in the search criteria, the search unit 108 retrieves measurement data having a patient name or a patient ID that matches the patient name or the patient ID specified by the search criteria. If taken time and a patient name are specified in the search criteria, the search unit 108 retrieves measurement data having a patient name or a patient ID that matches the patient name or the patient ID specified by the search criteria in a taken time range specified by the search criteria. For example, the search unit 108 makes a retrieval from another device connected via a network (e.g., a CT device, a vendor-neutral archive (VNA) or a picture archiving and communication system (PACS)), a storage device 100B (if measurement data are stored therein), or the like.

(Display Screen)

Figure 10:
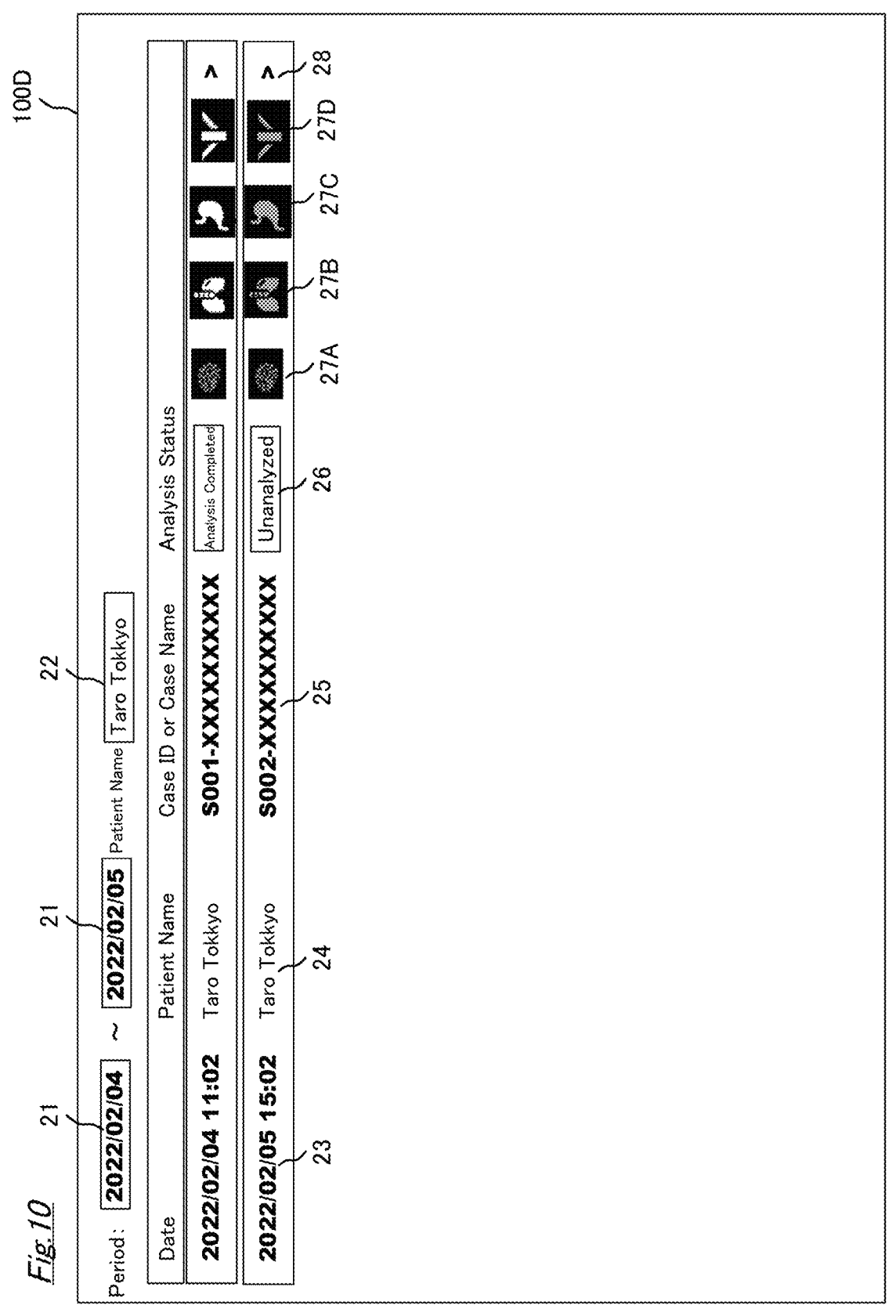

FIG. 10 is a diagram showing an example of a screen of a search result displayed on the display device 100D by the display unit 106 of the server 1.

As shown in FIG. 10, a search result by the search unit 108 is displayed in a list form on the display device 100D. Search criteria (a period 21 and a patient name 22) are displayed at an upper portion of the screen shown in FIG. 10. Date and time 23, a patient name 24, a case ID 25 (or case name), an analysis status 26, icons 27A-27D, and a transition button 28 are displayed for each row of the list of the search result at a lower portion of the screen shown in FIG. 10.

The display unit 106 displays the date and time 23, the patient name 24, and the case ID 25 based on information provided to the measurement data.

The display unit 106 displays the analysis status 26 and the icons 27A-27D based on analysis results outputted by the first and second disease identification models.

The display unit 106 displays the analysis status 26 in different manners depending on whether or not analysis has been made by the first and second disease identification models. For example, if analysis has been completed, the display unit 106 displays the words of "Analysis Completed" and turns on a light of the analysis status 26 (hereinafter referred to as a light-on display mode). If analysis has not been made, the display unit 106 displays the words of "Unanalyzed" and turn off the light of the analysis status 26 (hereinafter referred to as a light-off display mode). The displayed contents of the analysis status 26 are not limited to this example. For example, if analysis is being made, the display unit 106 may display the word of "Analyzing."

The icons 27A-27D correspond to respective body portions of a patient. (In this example, the icon 27A corresponds to a head, the icon 27B to a breast, the icon 27C to an abdomen, and the icon 27D to a pelvic part.) Body portions of a patient may be classified in more detail. In such a case, the number of corresponding icons increases.

The display unit 106 displays the icons 27A-27D in different manners depending on presence of measurement data for a head, a breast, an abdomen, or a pelvic part in a plurality of CT sliced images acquired by the first acquisition unit 103 and analysis results. For example, as a result of analysis, the display unit 106 displays icons corresponding to body portions having no measurement data in the light-off display mode. The display unit 106 displays icons corresponding to body portions having measurement data in the light-on display mode. In the example illustrated in FIG. 10, since there were no measurement data for a head in the row of "Analysis Completed" (for example, a head was not taken), the icon 27A is displayed in the light-off display mode while the other icons 27B-27D, which correspond to other body portions, are displayed in the light-on display mode. In the row of "Unanalyzed," since no analysis has been made on measurement data (i.e., identification of body portions included in a plurality of CT sliced images has not yet been made), the icons 27A-27D corresponding to all body portions are displayed in the light-off display mode.

The display unit 106 displays the icons 27A-27D in different manners depending on the analysis results of measurement data of a head, a breast, an abdomen, and a pelvic part (e.g., absence of a disease, presence of a disease (mild disease), or presence of a disease (severe disease)). For example, if no disease has been found at a body portion corresponding to an icon, the display unit 106 displays the icon in the light-off display mode. If a disease (mild disease) has been found, the display unit 106 displays the icon in the light-on display mode with yellow. If a disease (severe disease) has been found, the display unit 106 displays the icon in the light-on display mode with red. Thus, the server 1 displays analysis results of measurement data corresponding to a plurality of cases (for example, CT images of different patients or CT images of the same patient taken on different dates) in one screen. Furthermore, the server 1 displays a severity for each of the body portions as an analysis result of the case displayed in this screen. With such display, a user can recognize diseased body portions and severities of a plurality of cases in the same screen. Thus, visibility of the list of information is enhanced, and comparison of a plurality of cases is facilitated. The described manners for display are presented by way of example. Information may be displayed in another manner. For example, the server 1 may display a summary of the analysis results of cases for which analysis has been completed (e.g., a synthetic severity of the whole body of a patient) in addition to the information illustrated in FIG. 10. Pieces of the information illustrated in FIG. 10 may be displayed in a different location and in a different order.

The transition button 28 is an icon for changing a screen. If the analysis status 26 for a certain case is "Analysis Completed," the display unit 106 changes the screen to a screen showing an analysis result according to user's operation of selecting the transition button 28 that corresponds to that case. If the analysis status 26 for a certain case is "Unanalyzed," the display unit 106 changes the screen to an analysis screen and to a screen showing an analysis result after completion of the analysis according to user's operation of selecting the transition button 28 that corresponds to that case.

Figure 11:
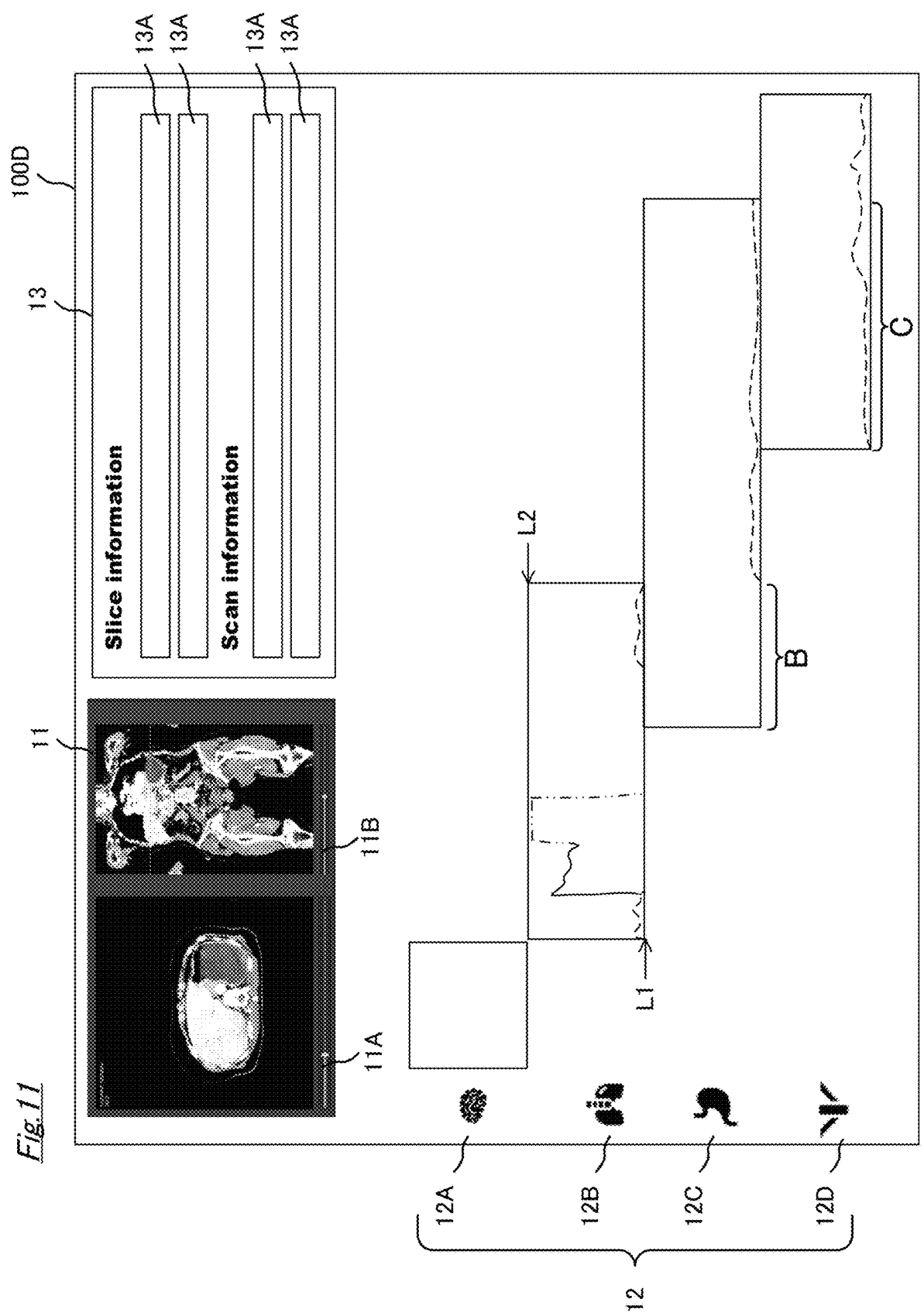
FIG. 11 is a diagram showing an example of a screen displayed on a display device of a server according to Variation 2 of the embodiment of the present invention.

FIG. 11 is a diagram showing an example of an analysis result display screen displayed on the display device 100D in a first form by the display unit 106 of the server 1, more specifically an example of a screen displayed when a display size of the first display area 11, which is a viewer component for displaying measurement data (image data) acquired by the first acquisition unit 103, is less than a threshold. In the following description, configurations that differ from the configurations described with reference to FIG. 4 will be described, and repetitive explanations thereof will be omitted herein.

As shown in FIG. 11, the display unit 106 is configured to display measurement data (image data) acquired by the first acquisition unit 103 in the first display area 11 as a viewer component, to display identification results acquired from the first disease identification model 104A by the second acquisition unit 105 in the second display area 12 as a timeline component, and to display identification results acquired from the second disease identification model 104B by the second acquisition unit 105 in the third display area 13 as an information component. In the example illustrated in FIG. 11, there is no fourth display area 14, which is a meta component for displaying an overall severity of a patient, icons for other operations, and the like. Nevertheless, a fourth display area 14 may be displayed.

The display unit 106 is configured to display identification results of measurement data for each of the classifications of the body portions in the second display area 12 in a manner corresponding to severities of diseases and accuracies (probabilities) with which a disease is present. The display unit 106 is configured to display line graphs each showing an accuracy of a disease that has been determined based on the measurement data with different colors or patterns corresponding to a severity of a disease. (In the example illustrated in FIG. 11, a "mild disease" corresponds to a dashed line, and a "severe disease" corresponds to a solid line. However, the line pattern is not limited to this example.) In the example illustrated in FIG. 11, a lower portion of each of the strips (a lower line L1) corresponds to an accuracy of "0" (a probability of 0%), whereas an upper portion of each of the strips (an upper line L2) corresponds to an accuracy of "1" (a probability of 100%). Specifically, as a value of a line graph is closer to the upper line L2 at any display position in the horizontal direction of the screen, a possibility that any disease is present at a body portion of a patient that corresponds to the display position increases. Furthermore, if a line graph is drawn by a solid line at the display position, then a user can recognize that the disease at that body portion is a severe disease. Instead of line graphs, other types of graphs such as bar graphs may be used to display disease accuracies. Thus, the display unit 106 is configured to display disease accuracies and severities at respective locations of a patient for each of the classifications of the body portions. Therefore, more information than the displayed example illustrated in FIG. 4 can be displayed, so that a user can readily recognize a physical condition of a patient in detail. FIG. 4 illustrates a display example showing a severity for each of body portions, whereas FIG. 11 illustrates a display example showing a severity and a disease accuracy for each of the body portions. Nevertheless, the display unit 106 may display a disease accuracy but not a severity for each of body portions.

As described in connection with FIG. 4, the body portions do not necessarily need to be displayed in the order of the "head 12A," the "breast 12B," the "abdomen 12C," and the "pelvic part 12D." The "head 12A," the "breast 12B," the "abdomen 12C," and the "pelvic part 12D" may be displayed in any order. For example, if the number of rows of the strips increases, confirmation of those strips may take more time. In such a case, the display unit 106 may sort the strips according to severities acquired from the first disease identification model 104A, so that the strips are displayed from the top in the descending order of severities. This sorted display allows a user to set a higher priority to a more dangerous portion to confirm a symptom or the like. The display order of the strips is not limited to the above example (severity order). For example, the strips may be sorted and displayed in an order corresponding to body portions or in a variously sorted order such as with only external injuries or with only internal diseases. For example, the display unit 106 may sort the respective strips according to a maximum value or an average value of disease accuracies of the respective body portions, so that the strips are displayed from the top in the descending order of maximum values or average values of disease accuracies. A user may specify how to sort the strips.

As described in connection with FIG. 4, simple classifications of body portions include a head, a breast, an abdomen, and a pelvic part in the present embodiment. For example, if the "breast" is subdivided into a "breast external injury" and a "breast internal disease" to provide multilayered classifications, the classifications 12A-12D illustrated in FIG. 11 are also displayed in a multilayered manner. In other words, the screen illustrated in FIG. 11 is provided by way of example of the embodiment. When the classifications of body portions are multilayered, the multilayered classifications are displayed in the second display area 12 of the display device 100D. Multilayered classifications include various patterns: For example, each of the classifications of the head, the breast, and the abdomen may be subdivided into an external injury and an internal disease. The classification of the abdomen may be subdivided into a liver and a stomach. The classification of the breast may be subdivided into a heart and lungs. The subdivision is not limited to the above examples. In another pattern, a row strip for a specific disease, such as presence of a COVID disease in a lung field, may be added. Thus, although the second display area 12 of FIG. 11 includes four rows of a head, a breast, an abdomen, and a pelvic part, the number of rows displayed in the second display area 12 of FIG. 11 varies according to the number of extreme emergency models corresponding to the subdivided levels.

The display unit 106 is also configured to display identification results (including treatment plans) acquired from the second disease identification model 104B by the second acquisition unit 105 in the third display area 13. In the example illustrated in FIG. 11, the display unit 106 displays a group of display frames 13A for each type of measurement data (for example, slice data, scan data, etc.).

Figure 12:
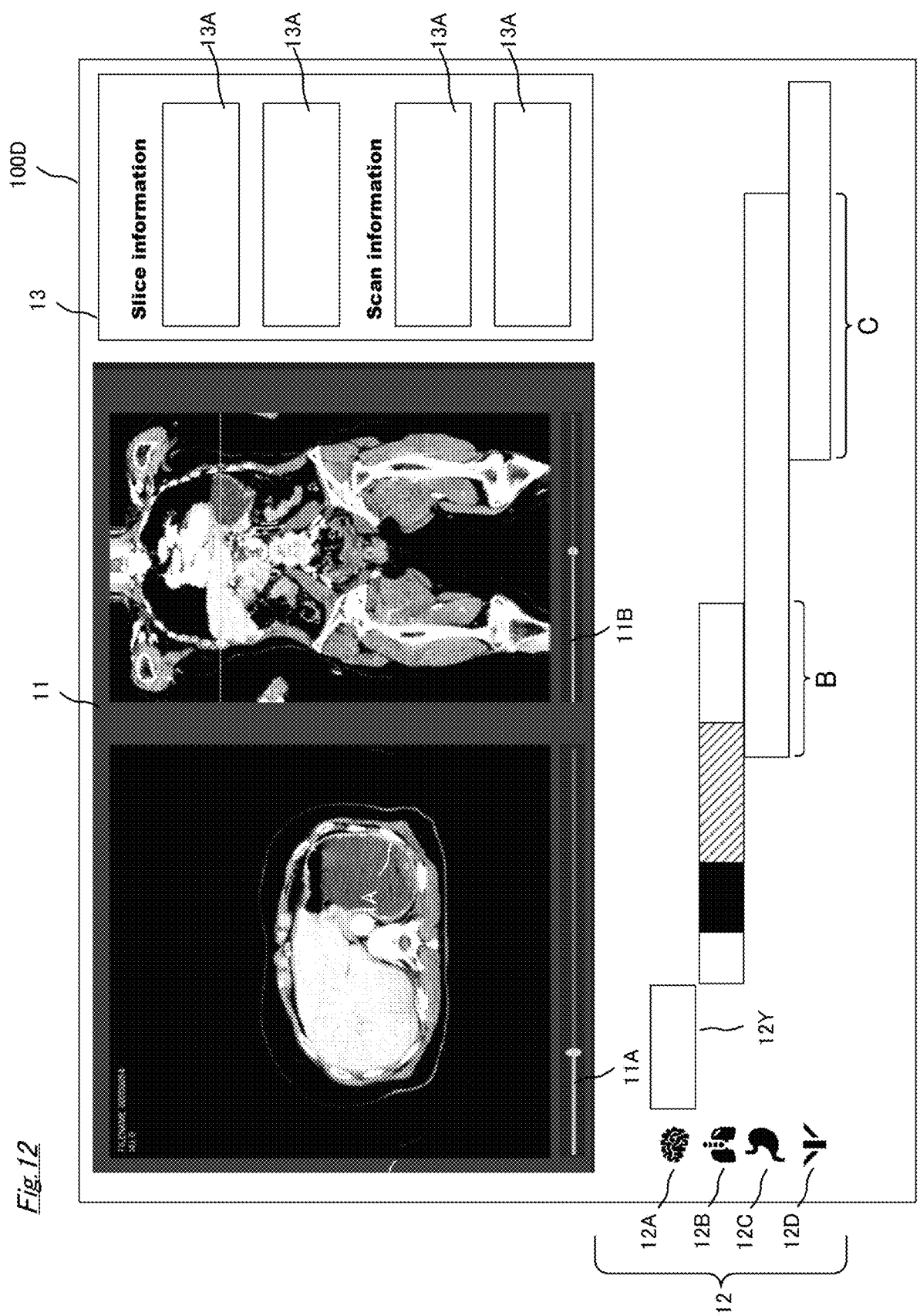
FIG. 12 is a diagram showing an example of a screen displayed on a display device of a server according to Variation 2 of the embodiment of the present invention.

FIG. 12 is a diagram showing an example of an analysis result display screen displayed on the display device 100D in a second form by the display unit 106 of the server 1, more specifically an example of a screen displayed when a display size of the first display area 11, which is a viewer component for displaying measurement data (image data) acquired by the first acquisition unit 103, is less than a threshold. In the following description, configurations that differ from the configurations described with reference to FIG. 4 will be described, and repetitive explanations thereof will be omitted herein.

As shown in FIG. 12, the display unit 106 is configured to display measurement data (image data) acquired by the first acquisition unit 103 in the first display area 11 as a viewer component, to display identification results acquired from the first disease identification model 104A by the second acquisition unit 105 in the second display area 12 as a timeline component, and to display identification results acquired from the second disease identification model 104B by the second acquisition unit 105 in the third display area 13 as an information component. In the example illustrated in FIG. 12, there is no fourth display area 14, which is a meta component for displaying an overall severity of a patient, icons for other operations, and the like. Nevertheless, a fourth display area 14 may be displayed.

As with the example illustrated in FIG. 4, the display unit 106 is configured to display identification results for each of the classifications of the body portions in the second display area 12 in a manner corresponding to severities of diseases.

As with the example illustrated in FIG. 11, the display unit 106 is also configured to display identification results (including treatment plans) acquired from the second disease identification model 104B by the second acquisition unit 105 in the third display area 13.

In this variation, the server 1 changes the display size of the first display area 11 according to user's operation and switches between the screen illustrated in FIG. 11 and the screen illustrated in FIG. 12 according to the display size. However, the switching conditions for the screens are not limited to this example. For example, the server 1 may display a screen switch button in a screen and may switch between the screen illustrated in FIG. 11 and the screen illustrated in FIG. 12 according to user's operation to the button.

(Information Processing)

FIG. 13 is a flow chart showing an example of a search process executed by the server 1 according to Variation 2 of the embodiment. An example of a search process executed by the server 1 will be described below with reference to FIG. 13.

(Step S401)

The input receiver 102 of the server 1 receives search criteria, such as taken time or a patient name.

(Step S402)

The search unit 108 of the server 1 retrieves measurement data that meet the search criteria received by the input receiver 102. The first acquisition unit 103 of the server 1 acquires the measurement data retrieved by the search unit 108. The search process by the search unit 108 has been described above, and repetitive explanations thereof will be omitted herein.

(Step S403)

The display unit 106 of the server 1 displays search results from the search unit 108 in a list form (see FIG. 10).

(Step S404)

When the input receiver 102 of the server 1 receives selection of the transition button 28, the server 1 determines whether or not the analysis status 26 is "unanalyzed." If the analysis status 26 is "unanalyzed" (YES), the server 1 executes a process of Step S405. If the analysis status 26 is not "unanalyzed" (NO), the server 1 executes a process of Step S406.

(Step S405)

The display unit 106 of the server 1 changes the display screen to an analysis screen. Analysis of measurement data starts with use of the first disease identification model 104A and the second disease identification model 104B. After the analysis, the display unit 106 changes the screen to a screen showing analysis results.

(Step S406)

The display unit 106 of the server 1 determines whether or not the display size of the first display area 11 that has been received by the input receiver 102 is less than a threshold. If the display size is less than the threshold (YES), the server 1 executes a process of Step S407. If the display size is not less than the threshold (NO), the server 1 executes a process of Step S408.

(Step S407)

The display unit 106 of the server 1 displays analysis results of the measurement data in the first form (see FIG. 11).

(Step S408)

The display unit 106 of the server 1 displays analysis results of the measurement data in the second form (see FIG. 12).

Any of the above embodiments and variations thereof is presented by way of example of embodying the present invention. It should not be understood that the technical scope of the present invention is limited to those embodiments and variations thereof. Specifically, the present invention may be implemented in a wide variety of manners without departing from the spirit and primary features of the present invention.

DESCRIPTION OF REFERENCE NUMERALS AND SIGNS

1 Server (information processing apparatus)
100A Communication IF
100B Storage device
100C Input device
100D Display device
100E CPU
101 Storage device controller
102 Input receiver
103 First acquisition unit
104A First disease identification model
104B Second disease identification model
105 Second acquisition unit
106 Display unit
107 Output unit
108 Search unit

The invention claimed is:

1. An information processing apparatus comprising:
a processor; and
a storage device communicatively connected to the processor, the storage device having instructions that, when executed by the processor, cause the processor to perform steps of:
  acquiring an identification result on a disease that has been identified based on measurement data on a physical condition of a plurality of body portions of a patient; and
  displaying a first image in a first display area and a second image in a second display area separated from the first display area on a display device,
wherein the identification result includes information indicative of at least one of a severity of the disease and an accuracy of presence of the disease for each of the plurality of body portions of the patient,
wherein the first image represents the measurement data, and
wherein the second image includes an image object that is a strip of a graph having a first axis and a second axis, the first axis corresponding to a location in one of the plurality of body portions and the second axis corresponding to the accuracy of presence of the disease at the location in the one of the plurality of body portions.

2. The information processing apparatus as recited in claim 1, wherein the identification result further includes information indicative of presence of any disease.

3. The information processing apparatus as recited in claim 1, wherein the second image includes a plurality of image objects corresponding respectively to the plurality of body portions of the patient,
wherein each of the plurality of image objects represents at least one of the severity of the disease and the accuracy of presence of the disease across a plurality of measurement locations included in the plurality of body portions corresponding to each of the plurality of image objects.

4. The information processing apparatus as recited in claim 3, wherein the plurality of image objects are displayed in an order of priority based on the identification result.

5. The information processing apparatus as recited in claim 3, wherein the measurement data are obtained by measurement using computerized tomography or magnetic resonance imaging,
wherein each of the plurality of image objects includes a plurality of segments located adjacent to each other so as to correspond to the plurality of measurement locations in the measurement.

6. The information processing apparatus as recited in claim 3, wherein each of the plurality of image objects is a belt-shaped object,
wherein each of the plurality of image objects is displayed in a form corresponding to the severity of the disease at a corresponding one of the plurality of measurement locations.

7. The information processing apparatus as recited in claim 3, wherein each of the plurality of image objects include a graph,
wherein a value of the graph represents the accuracy of presence of the disease at a corresponding one of the plurality of measurement locations,
wherein a color or a pattern of the graph represents the severity of the disease at a corresponding one of the plurality of measurement locations.

8. The information processing apparatus as recited in claim 3, wherein
the first image displayed in the first display area is switched according to a location of user's operation to the second image displayed in the second display area.

9. The information processing apparatus as recited in claim 3, wherein
a form of the second image displayed in the second display area is switched according to an input specifying a display size of the first display area.

10. The information processing apparatus as recited in claim 1, wherein the step of acquiring comprises acquiring a plurality of identification results corresponding respectively to a plurality of disease cases,
wherein the second image indicates disease information on each of body portions for each of the plurality of disease cases.

11. The information processing apparatus as recited in claim 10, wherein the instructions cause the processor to perform a step of receiving a search criterion,
wherein the step of acquiring comprises acquiring the identification result corresponding to each of the plurality of disease cases that meets the search criterion received by the step of receiving.

12. The information processing apparatus as recited in claim 1,
wherein the second image represents both of the severity of the disease and the accuracy of presence of the disease.

13. An information processing method comprising:
an acquisition step of acquiring an identification result on a disease that has been identified based on measurement data on a physical condition of a plurality of body portions of a patient;
a display step of displaying a first image in a first display area and a second image in a second display area separated from the first display area on a display device,
wherein the identification result includes information indicative of at least one of a severity of the disease and an accuracy of presence of the disease for each of the plurality of body portions of the patient, wherein the first image represents the measurement data, and wherein the second image includes an image object that is a strip of a graph having a first axis and a second axis, the first axis corresponding to a location in one of the plurality of body portions and the second axis corresponding to the accuracy of presence of the disease at the location in the one of the plurality of body portions.

14. The information processing method as recited in claim 13, wherein the identification result further includes information indicative of presence of any disease.

15. The information processing method as recited in claim 13, wherein the second image includes a plurality of image objects corresponding respectively to the plurality of body portions of the patient, wherein each of the plurality of image objects represents at least one of the severity of the disease and the accuracy of presence of the disease across a plurality of measurement locations included in the body portion corresponding to the image object.

16. A non-transitory computer readable medium storing a program for causing a computer to execute an information processing method comprising:

an acquisition step of acquiring an identification result on a disease that has been identified based on measurement data on a physical condition of a plurality of body portions of a patient; and a display step of displaying a first image in a first display area and a second image in a second display area separated from the first display area on a display device, wherein the identification result includes information indicative of at least one of a severity of the disease and an accuracy of presence of the disease for each of the plurality of body portions of the patient, wherein the first image represents the measurement data, wherein the second image includes an image object that is a strip of a graph having a first axis and a second axis, the first axis corresponding to a location in one of the plurality of body portions and the second axis corresponding to the accuracy of presence of the disease at the location in the one of the plurality of body portions.

* * * * *